United States Patent [19]

Berg

[11] Patent Number: 5,800,681
[45] Date of Patent: Sep. 1, 1998

[54] SEPARATION OF ETHANOL, ISOPROPANOL AND WATER MIXTURES BY EXTRACTIVE DISTILLATION

[76] Inventor: Lloyd Berg, 1314 S. 3rd Ave., Bozeman, Mont. 59715

[21] Appl. No.: 845,107

[22] Filed: Apr. 21, 1997

[51] Int. Cl.$^6$ .................... B01D 3/40; C07C 29/84
[52] U.S. Cl. .................... 203/57; 203/18; 203/19; 203/58; 203/62; 203/64; 203/65; 203/68; 203/69; 568/913; 568/916
[58] Field of Search .................... 203/57, 18, 58, 203/19, 62, 64, 65, 68, 69, 70, 63, DIG. 13; 568/913, 916

[56] References Cited

U.S. PATENT DOCUMENTS

| | | | |
|---|---|---|---|
| 2,375,036 | 5/1945 | Dunn et al. | 203/57 |
| 3,898,291 | 8/1975 | Darsi et al. | 203/99 |
| 3,960,672 | 6/1976 | Ester | 203/18 |
| 4,428,798 | 1/1984 | Zud Kevitch et al. | 203/19 |
| 4,559,109 | 12/1985 | Lee et al. | 203/19 |
| 4,566,948 | 1/1986 | Berg et al. | 203/58 |
| 4,636,284 | 1/1987 | English et al. | 203/64 |
| 4,710,274 | 12/1987 | Berg et al. | 203/60 |
| 5,084,142 | 1/1992 | Berg et al. | 568/916 |
| 5,085,739 | 2/1992 | Berg et al. | 568/916 |
| 5,449,440 | 9/1995 | Rescalli et al. | 203/18 |

FOREIGN PATENT DOCUMENTS

| | | | |
|---|---|---|---|
| 525258 | 5/1956 | Canada | 203/18 |
| 762974 | 12/1956 | United Kingdom | 203/18 |

*Primary Examiner*—Virginia Manoharan

[57] ABSTRACT

Ethanol, isopropanol and water cannot be separated from each other by distillation or rectification because of minimum azeotropes. They are readily separated by extractive distillation. Effective agents are: dimethylsulfoxide for ethanol, phenol for isopropanol.

2 Claims, No Drawings

5,800,681

SEPARATION OF ETHANOL, ISOPROPANOL AND WATER MIXTURES BY EXTRACTIVE DISTILLATION

FIELD OF THE INVENTION

This invention relates to a method of separating ethanol, isopropanol and water from mixtures thereof using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Ethanol and isopropanol form minimum boiling azeotropes with water and a mixture of these three form a minimum boiling ternary azeotrope and cannot be separated from each other by conventional distillation or rectification. Extractive distillation would be an attractive method of effecting the separation of these three if agents can be found that (1) will create a large apparent relative volatility among these three and (2) are easy to recover. Table 2 shows the relative volatility required to obtain 99% purity. With an agent giving a relative volatility of 2.5, only 14 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.5 | 22 | 30 |
| 2.0 | 12 | 16 |
| 2.5 | 10 | 14 |

OBJECTIVE OF THE INVENTION

The object of this invention is to provide a process or method of extractive distillation that will enhance the relative volatility of ethanol, isopropanol and water in their separation in a rectification column. It is a further object of this invention to identify organic compounds which in addition to the above constraints, are stable, can be separated from ethanol, isopropanol and water and recycled to the column with little decomposition.

SUMMARY OF THE INVENTION

The objects of this invention are provided by a process for separating ethanol, isopropanol and water which entails the use of certain organic compounds as the agent in extractive distillation.

TABLE 3

Effective Extractive distillation Agents For Separating Ethanol From Ethanol - Isopropanol - Water Mixtures

| | Relative Volatility | | |
|---|---|---|---|
| Compound | EtOH/PrOH | EtOH/Water | PrOH/Water |
| Diethylene glycol | 2.3 | 1.4 | 1.6 |
| Dimethylsulfoxide | 2.6 | 1.35 | 2.0* |
| 4-Methyl-2-pentanone | 3.5 | 1.55 | 2.2 |
| Polyethylene glycol 400 | 1.5 | 1.35 | 1.15 |

*Water/PrOH

TABLE 4

Effective Extractive Distillation Agents For Separating Isopropanol From Isopropanol - Ethanol - Water Mixtures

| | Relative Volatility | | |
|---|---|---|---|
| Compound | PrOH/EtOH | PrOH/Water | EtOH/Water |
| Ethyl benzene | 1.45 | 2.0 | 1.4 |
| Toluene | 1.6 | 2.3 | 1.35 |
| p-Xylene | 1.7 | 2.6 | 1.5 |
| Heptane | 1.35 | 2.1 | 1.4 |
| Phenol | 1.53 | 2.1 | 1.35 |
| 2-tert. Butyl phenol | 1.35 | 2.1 | 1.5 |

DETAILED DESCRIPTION OF THE INVENTION

In a mixture comprising ethanol, isopropanol and water there are two binary azeotropes, ethanol—water and isopropanol—water, boiling two degrees apart and making it impossible to separate by conventional distillation or rectification.

I have discovered that certain organic compounds will greatly improve the relative volatility between ethanol, isopropanol and water and permit the separation by rectification when employed as the agent in extractive distillation. Table 3 lists the compounds which are effective in: separating ethanol from isopropanol and water by extractive distillation. They are diethylene glycol, dimethylsulfoxide, 4-methyl-2-pentanone and polyethylene glycol 400. Table 4 lists the compounds which are effective in separating isopropanol from ethanol and water by extractive distillation. They are ethyl benzene, toluene, p-xylene, heptane, phenol and 2-tert-butyl phenol.

THE USEFULNESS OF THE INVENTION

The usefulness of this invention can be demonstrated by referring to the data presented in Tables 1, 2, 3 and 4. All of the successful agents show that ethanol, isopropanol and water can be separated from each other by means of extractive distillation in a rectification column and that the ease of separation as measured by relative volatility is considerable.

WORKING EXAMPLES

1. Fifty grams of an ethanol, isopropanol, water mixture and 50 grams of dimethylsulfoxide were charged to a vapor-liquid equilibrium still and refluxed for two hours. The vapor composition was 29.4% water, 64.0% ethanol and 6.6% isopropanol, the liquid composition was 32.5% water, 52.8% ethanol and 14.7% isopropanol. This is a relative volatility of ethanol/isopropanol of 2.6, of ethanol/water of 1.35% and of isopropanol/water of 2.0.

2. Fifty grams of an ethanol, isopropanol, water mixture and 50 grams of phenol were charged to a vapor-liquid equilibrium still and refluxed for four hours. The vapor composition was 22.5% water, 58.9% ethanol and 18.6% isopropanol, the liquid composition was 30.2% water, 57.4% ethanol and 12.4% isopropanol. This is a relative volatility of isopropanol/ethanol of 1.53 of isopropanol/water of 2.1 and of ethanol/water of 1.35.

I claim:

1. A method for recovering ethanol from a mixture consisting of ethanol, isopropanol and water which consists essentially of distilling said mixture of ethanol, isopropanol and water in the presence of an extractive distillation agent, recovering the ethanol as overhead product and obtaining the isopropanol, water and the extractive distillation agent as bottoms product, wherein said extractive distillation agent consists of one material selected from the group consisting of diethylene glycol, dimethylsulfoxide, 4-methyl-2-pentanone and polyethylene glycol 400.

2. A method for recovering isopropanol from a mixture consisting of isopropanol, ethanol and water which consists essentially of distilling said mixture in the presence of an extractive distillation agent, recovering the isopropanol as overhead product and obtaining the ethanol, water and the extractive distillation agent as bottoms product, wherein said extractive distillation agent consists of one material selected from the group consisting of ethyl benzene, toluene, p-xylene, heptane, phenol and 2-tert-butyl phenol.

* * * * *